(12) United States Patent
Palma et al.

(10) Patent No.: US 10,568,694 B2
(45) Date of Patent: Feb. 25, 2020

(54) METHOD AND SYSTEM FOR PERFORMING A GUIDED BIOPSY USING DIGITAL TOMOSYNTHESIS

(71) Applicant: GENERAL ELECTRIC COMPANY, Schenectady, NY (US)

(72) Inventors: Giovanni John Jacques Palma, Issy les Moulineaux (FR); Remy Andre Klausz, Neuilly sur Seine (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 259 days.

(21) Appl. No.: 14/693,863

(22) Filed: Apr. 22, 2015

(65) Prior Publication Data

US 2016/0310215 A1 Oct. 27, 2016

(51) Int. Cl.
*A61B 6/12* (2006.01)
*A61B 34/10* (2016.01)
(Continued)

(52) U.S. Cl.
CPC .............. *A61B 34/10* (2016.02); *A61B 6/025* (2013.01); *A61B 6/0414* (2013.01); *A61B 6/12* (2013.01);
(Continued)

(58) Field of Classification Search
CPC .......... A61B 10/0233; A61B 2034/107; A61B 34/10; A61B 6/025; A61B 6/04;
(Continued)

(56) References Cited

U.S. PATENT DOCUMENTS 4,798,212 A 1/1989 Arana
4,875,478 A 10/1989 Chen
(Continued)

FOREIGN PATENT DOCUMENTS

DE 102012200207 B3 5/2013
WO 2007095330 A2 8/2007
(Continued)

OTHER PUBLICATIONS

International Search Report and Written Opinion for PCT/US2016/028569, dated Aug. 22, 2016, 13 pages.
(Continued)

*Primary Examiner* — Mark D Remaly
(74) *Attorney, Agent, or Firm* — Fletcher Yoder, P.C.

(57) ABSTRACT

A method and system for performing a biopsy guided by a 3D image of the object obtained from digital tomosynthesis is performed. The method includes applying a compression paddle to an object; performing a tomosynthesis scan; reconstructing at least a portion of the scan; locating a lesion using a displayed or reprojected marker to determine a location of the lesion; correlating the location of the lesion in the scan to a marker on the compression paddle or tool holder; and proposing a needle entry point of a biopsy tool based off of the correlation so that a needle or penetration device will effectively reach the lesion or target if it is inserted at the proposed entry point. A system for performing a biopsy is further disclosed. In one embodiment, the system comprises: a tomosynthesis imaging apparatus for performing a tomosynthesis scan comprising an x-ray source and an x-ray detector; at least one marker; a compression paddle; a controller; and a display screen for displaying at least a portion of a reproduction of a tomosynthesis scan generated by the imaging apparatus, wherein (i) the at least one marker is displayed on the reproduction, the marker being used to (Continued)

determine a lesion location or target, and (ii) the controller correlates the lesion location or target with the at least one marker and generates a proposed needle entry point based on the correlation so that a needle or penetration device will effectively reach the lesion or target if it is inserted at the proposed entry point.

13 Claims, 13 Drawing Sheets

(51) Int. Cl.
  *A61B 6/00* (2006.01)
  *A61B 90/00* (2016.01)
  *A61B 10/02* (2006.01)
  *A61B 6/04* (2006.01)
  *A61B 6/02* (2006.01)

(52) U.S. Cl.
  CPC .......... *A61B 6/502* (2013.01); *A61B 10/0233* (2013.01); *A61B 90/39* (2016.02); *A61B 6/461* (2013.01); *A61B 6/5205* (2013.01); *A61B 2034/107* (2016.02)

(58) Field of Classification Search
  CPC .......... A61B 6/0414; A61B 6/12; A61B 6/461; A61B 6/502; A61B 6/5205; A61B 90/39
  See application file for complete search history.

(56) References Cited

U.S. PATENT DOCUMENTS

| 8,532,745 | B2 | 9/2013 | DeFreitas et al. |
| 2008/0045833 | A1 | 2/2008 | Defreitas et al. |
| 2009/0171244 | A1* | 7/2009 | Ning .................. A61B 6/032 600/567 |
| 2011/0230758 | A1* | 9/2011 | Eichler .................. A61B 5/06 600/424 |
| 2013/0303895 | A1* | 11/2013 | Littrup .................. A61B 8/406 600/424 |
| 2014/0073913 | A1 | 3/2014 | Defreitas et al. |
| 2014/0303483 | A1 | 10/2014 | Schellenberg et al. |

FOREIGN PATENT DOCUMENTS

WO 2010102087 A1 9/2010
WO 2015044711 A1 4/2015

OTHER PUBLICATIONS

Wilson et al., "Comparison of Large-Core Vacuum-Assisted Breast Biopsy and Excision Systems", Recent Results in Cancer Research, vol. No. 173, Issue No. 23, Springer-Verlag Berlin Heidelberg, pp. 23-41, 2009.

* cited by examiner

METHOD AND SYSTEM FOR PERFORMING A GUIDED BIOPSY USING DIGITAL TOMOSYNTHESIS

BACKGROUND

The subject matter disclosed herein relates to a method and system for performing a biopsy of an object guided by a 3D image of the object obtained from digital tomosynthesis. More particularly, the disclosure relates to a simplified method and system for performing a guided breast biopsy using digital breast tomosynthesis.

Mammography is the principal method of identifying a lump or lesion found within a breast. Once a lesion is located, a biopsy is typically performed to obtain a tissue or cell sample, which allows for determination as to whether the lesion is benign or malignant. The biopsy may be performed through surgery or by inserting a needle into an object, such as a breast, and removing a sample using a needle and/or aspiration. Locating the lesion prior to the biopsy can be difficult, and various methods have been developed to aid in lesion location. Known methods of locating the lesion prior to a biopsy result in missed targets due to insufficient geometric accuracy. At this time, two methods of locating a lesion predominate, the first of which uses ultrasound, and the second of which relies on multiple images. In the first method, ultrasound is used to guide the needle or vacuum-assisted biopsy device to the target location of the lesion. In the second method, at least two images of the lesion visible under x-rays are taken at two known angles, and the x, y, and z coordinates of a point from the lesion's positions in the two angulated views is computed. Because the object may change shape, these past attempts at locating the lesion could involve multiple attempts at inserting the needle or the vacuum assisted biopsy tool, causing pain and discomfort to the patient.

Presently, devices have been developed to assist in positioning a tool using tomosynthesis. Digital Tomosynthesis provides a 3D image of a scanned object by taking x-ray images. For example, a breast may be compressed in a stationary position and x-ray images taken at multiple angles during a Digital Breast Tomosynthesis "DBT" scan. From this set of images a reconstruction is performed which generates an image or projections of the complete volume under the form of a large number of images representing cross-sections ("slices") of the object computed at small intervals, e.g. 1 mm or less. The slices can be examined to identify and locate the lesion within the breast. DBT imaging provides better visibility creating improved contrast and visibility.

Once a lesion is identified, current methods of determining an entry point for a biopsy tool involve identifying the coordinates of the target, including the depth the tool is to be inserted. Once the coordinates are determined, the coordinates are transferred to a stage. This stage is moved into place automatically if motorized or manually, and will direct the needle into the breast. The stage uses 3D coordinates of the target identified through analysis of the DBT images or stereotactic pair to move the biopsy device and needle to the proposed coordinates of the target. In known techniques, the needle location is verified before the breast biopsy is performed. Verification of the needle is accomplished by inserting the needle into the breast about two centimeters from the center of the target, due to the distance between the tip of the needle and the side window through which the biopsy is performed, and performing additional image scans or x-rays to verify the needle location relative to the target. After the needle location is verified by confirming it was inserted 2 cm from the target, the needle is then moved to the proposed location of the target, and the needle is inserted into the breast to reach the target. Once the needle is inserted into the location believed to correspond to the target, another scan or image is acquired to verify the needle has reached the lesion prior to any tissue being sampled.

A problem of the method discussed above is that it requires an explicit computation of the x-y-z coordinates of the target point and the transfer of these coordinates to the stage. An additional problem of the method discussed above is the size and weight of the stage, whether the stage is motorized or manual. The reliance on the stage, which positions the biopsy tool, can be complicated and can require a motor as well as a position display at a significant cost. The stage is also bulky and takes up valuable space in a facility where biopsy procedures may be performed.

Two dimension approaches have also been developed; however, a problem with the "2D-localization" approaches occurs when the image of an indicator disposed on the paddle forms a conic projection when superimposed on the lesion. In the current 2D approach, when the needle is pushed perpendicular to the paddle or detector, a systematic error results. Except for structures on the line perpendicular to the detector and intersecting the focal spot, the angulation of the beam will generate an error in the location of the paddle projecting on the same point of the detector as the target. This error can oftentimes cause the target to be missed. This problem is worsened if the needle is inserted at a significant angle.

SUMMARY

A method and system for performing a biopsy of an object guided by the 3D image of the object is disclosed. More particularly, embodiments of a method and system for performing a breast biopsy guided by a 3D image of a breast obtained from digital breast tomosynthesis ("DBT") are provided.

In the embodiments of the system and method disclosed herein, a DBT volume is reconstructed. From the reconstruction, a geometric relationship between at least a portion of the reconstructed 3D image and the path of the needle for a given entry point is determined. A transformation is applied to a real or schematic image of a tool holder or a currently displayed or visualized section of a DBT image in a manner that when the tool support is positioned in a location in coincidence with the image of the biopsy target, the biopsy tool will effectively reach the desired target. In an embodiment, the system and/or method may not require the transfer of coordinates corresponding to the lesion to a needle positioning stage, but instead uses or relies upon a graphical superimposition or reprojection of means to position a biopsy tool over a portion of the DBT image. After the graphical superimposition, the needle can be positioned with no reference to coordinates of the target. This is accomplished by an image of a tool holder being geometrically transformed and superimposed with at least one plane or slice of the lesion as selected by a user. By superimposing the tool holder, a position of a biopsy tool on the tool holder may be selected on the superimposed image, which directly corresponds to the tool holder enabling the lesion to be reached by the tool once positioned on the tool holder itself.

An embodiment provides a combined marker or grid between the DBT volume and the paddle, where a relationship is formed by correlating the marker or grid to the marker or grid that is superimposed or reproduced in the DBT volume, or where the relationship allows for extrapolation to the target location. In an embodiment, a grid is located just above the paddle and a real image or schematic image of the grid is transformed and superimposed with the image of a section of the reconstructed DBT volume. The biopsy can then be performed using a portion or an area defined by the paddle or tool holder directly registered with the DBT volume. The transformation consists of a reprojection, reproduction, overlay, or synthesis of the grid or marker on the DBT slices allowing the proper identification of the needle entrance point on the displayed images.

The system and method disclosed herein generates a coincidence of the location in the plane of the apertures or a tool holder with the location in the plane of the target. In an embodiment, this location or address of the target may be in the form of x and y coordinates or any other location identification system allowing a position of a target to be known; for example, a row and column coordinate system where an area or location is associated with or identified by a row and column designation, a grid having discrete squares, circles, polygons, or similar shapes, each shape identifiable within the boundaries or perimeter of the grid, or a concentric circular grid or target where locations are identified, for example by radial distance and circumferential degrees relative to the center. The location may be a precise point, an individual shape, space or an area, such as the area of a square on a grid, which may correspond to the area of a square on a grid of a tool holder, for example. In another example where x and y coordinates are used, the x and y coordinates of the plane of the apertures may be coordinated with the x and y coordinates of the plane of the target. The z coordinate may correspond to the depth a biopsy tool must be inserted to reach the target and can be identified based on the slice selected in the DBT reconstruction. This is accomplished by graphical representation of the visual references associated with the apertures in a graphic plane superimposed with the image of the relevant tomographic plane.

In one embodiment, a method is disclosed for using a tomosynthesis imaging system and at least one marker, which includes applying a compression paddle to an object to be scanned, performing a tomosynthesis scan on at least a portion of the object, reconstructing at least a portion of the tomosynthesis scan of the object on a display screen, wherein the at least one marker is visible on at least a portion of the reconstruction. The method further includes determining a location of the lesion based upon the at least one reprojected marker, correlating the location of the lesion based upon the at least one reprojected marker, and proposing a needle entry point of a biopsy tool using the correlation of the location of the lesion with the at least one marker.

In another embodiment, a system for performing a biopsy is disclosed, which includes a tomosynthesis imaging apparatus for performing a tomosynthesis scan comprising an x-ray source and an x-ray detector, at least one marker, a compression paddle, a controller, and a display screen for displaying at least a portion of a reproduction of the tomosynthesis scan. The system further includes where the controller displays the at least one marker on the reproduction, the marker being used to determine a lesion location, the controller correlating the lesion location with the at least one marker, and a needle entry point being proposed based upon the correlation.

In yet another embodiment, a system for performing a breast biopsy is disclosed, which includes a digital breast tomosynthesis imaging apparatus for performing a digital breast tomosynthesis scan comprising an x-ray source and an x-ray detector, at least one marker, a compression paddle, a controller, and a display screen for displaying at least a portion of a reproduction of the digital breast tomosynthesis scan. The Controller uses the at least one marker to display a grid on at least a portion of the digital breast tomosynthesis image where the grid is used to determine a lesion location that is correlated with the at least one marker, and a needle entry point is proposed based upon the correlation determined by the controller between the lesion location and the at least one marker.

BRIEF DESCRIPTION OF THE DRAWINGS

The operation of the inventive methods and systems will become apparent from the following description taken in conjunction with the drawings, in which.

DETAILED DESCRIPTION

Figure 1:
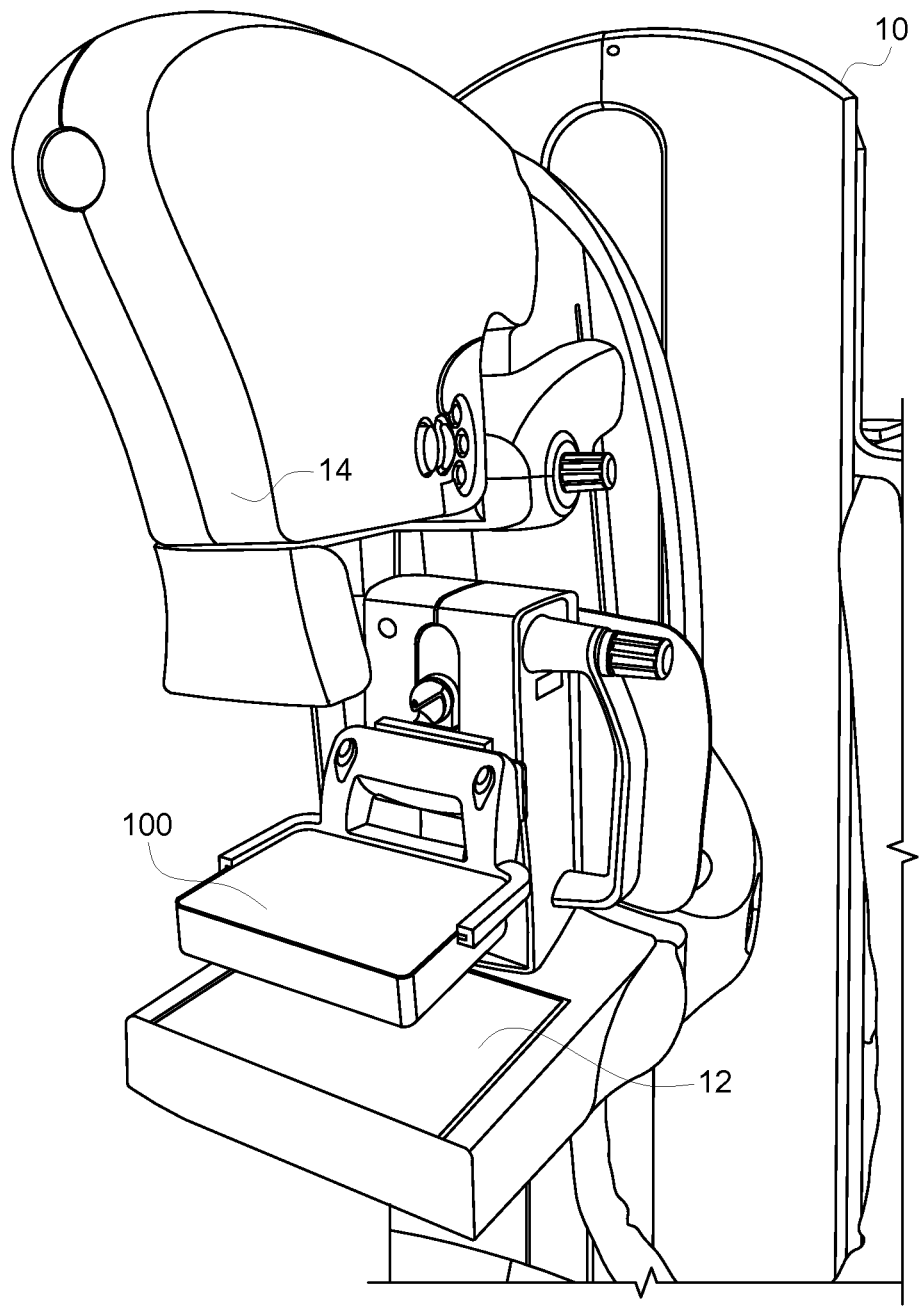
FIG. 1 illustrates an exemplary tomosynthesis apparatus.
Figure 2:
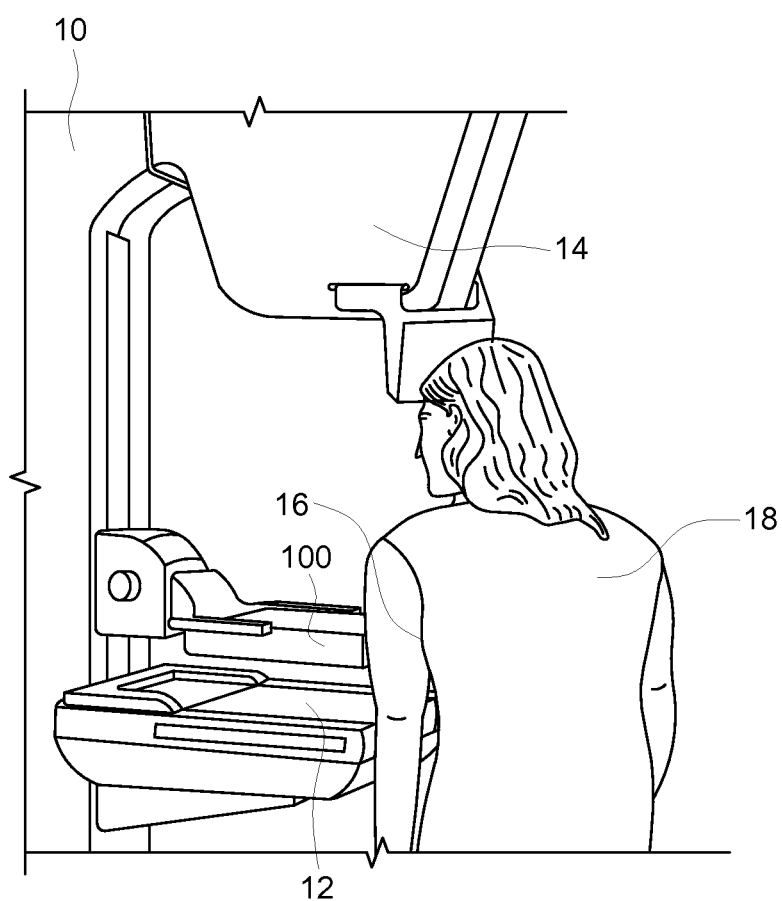
FIG. 2 illustrates an apparatus as applied to a patient undergoing a scan.

Referring to FIG. 1 and FIG. 2, an image of an exemplary tomosynthesis apparatus is shown. The tomosynthesis apparatus 10 of FIG. 1 is a digital breast tomosynthesis ("DBT") apparatus, and is supplied for exemplary purposes. It is to be understood that the systems and methods described herein may be applied to other similar uses in the field of x-ray imaging and tomography, and is not limited to the field of DBT or breast biopsies.

At least one advantage that may be realized from the use of the system described herein is that a biopsy needle or device can be accurately positioned at a low cost by using already-existing imaging machines, such as a DBT apparatus, without high cost modifications or attachments. Another advantage is that a visual superimposition of an image of a tool holder where a biopsy tool is positioned may be shown on a selected reconstructed plane or slice rather than explicitly generating coordinates of a target.

In an exemplary embodiment, a DBT apparatus includes a digital detector 12 and an x-ray source 14 used to project through an object 16 being scanned, such as a portion of a patient. The detector receives x-rays that pass through the object being scanned and produces digital signals relating to the intensity of the x-rays. The x-ray source may be in communication with a computer, processor and/or controller. In some embodiments, the x-ray source is in communication with a controller, which is in communication with a computer system. The computer system provides instructions to the controller, for example, to operate other systems and components, such as a gantry, which moves the x-ray source through a predetermined viewing range of viewing angles along an arcuate trajectory.

Referring to FIG. 2, an image of patient is shown positioned within an apparatus as described above with reference to FIG. 1. A patient 18 may stand, sit, or lay down during the biopsy procedure for a continuous period of time, which allows the breast to be scanned and biopsied with better accuracy. The period of time to complete the biopsy procedure as discussed herein may vary. In some instances, the procedure may take less than 10 minutes, less than 20 minutes, less than 30 minutes, or less than an hour. Throughout the procedure the breast or object should remain substantially stationary. This may be accomplished by using compression devices such as a compression paddle 100, a compression grid, a tool holder 200, or similar means to hold the breast in a substantially stationary position at least for the time when the breast is initially scanned to a time when the biopsy is performed. The compression paddle 100 may hold the breast still while providing apertures that allow for insertion of a biopsy tool, needle, core needle, or vacuum assisted core needle and the tool holder 200 or grid may be used to hold the biopsy tool or needle in place. The compression paddle 100 or the tool holder 200 may also serve to compress the object or breast to minimize the thickness traversed by x-rays.

Figure 3:
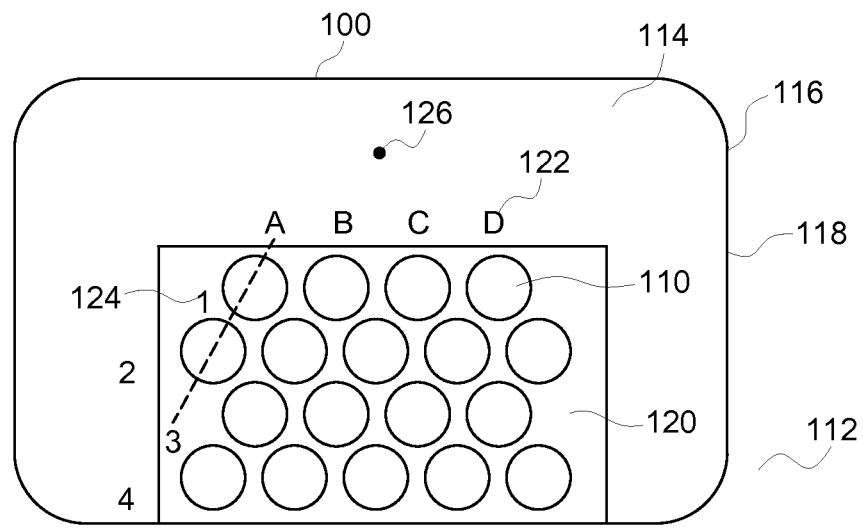
FIG. 3 illustrates a compression paddle having circular apertures.
Figure 4:
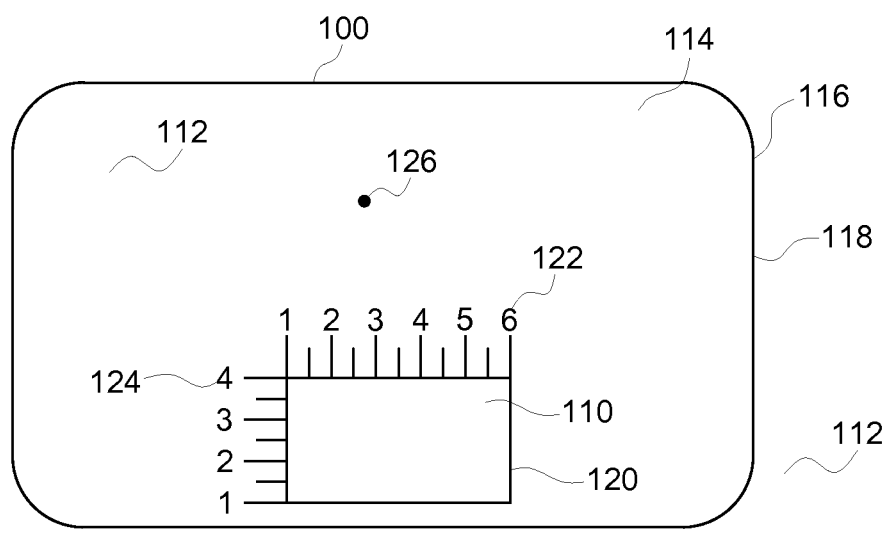
FIG. 4 illustrates a compression paddle having linear apertures.
Figure 5:
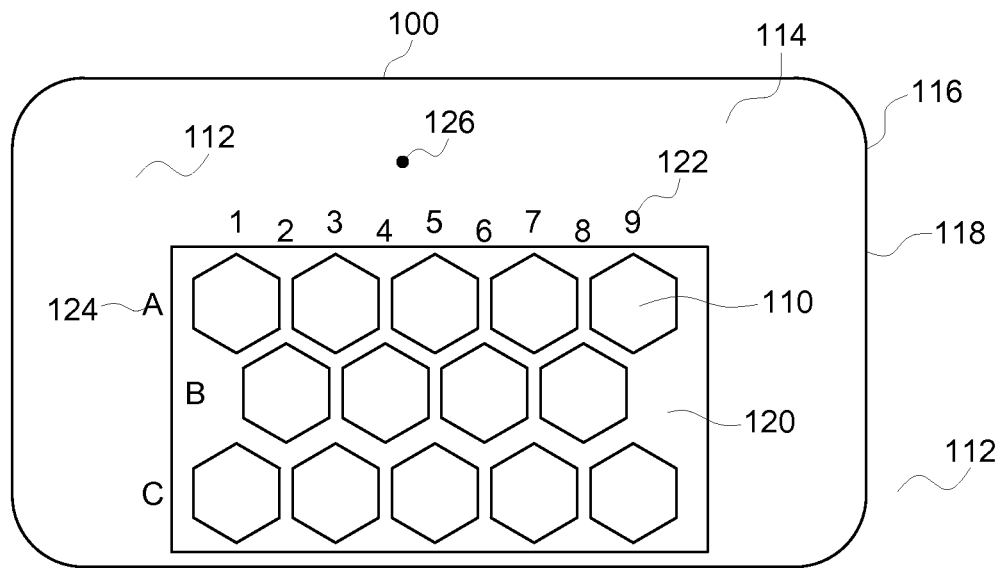
FIG. 5 illustrates a compression paddle having polygonal apertures.

Referring to FIG. 3, FIG. 4, and FIG. 5, exemplary embodiments of compression paddles that may be used with a tomosynthesis system to hold the breast in place during a procedure are shown. According to an embodiment, compression paddle 100 may be in the form of molded plastic, and include at least one aperture 110, which allows the needle of a biopsy tool to extend through the compression paddle 100. Alternatively, in circumstances where a biopsy tool or needle need not extend through compression paddle, such as when performing a lateral biopsy, the compression paddle 100 may not have any apertures. The compression paddle 100 may be in the form of any material that is rigid enough to hold a breast or object in place, but does not substantially interfere with the image acquisition of the tomosynthesis apparatus 10.

In an one embodiment, compression paddle 100 has a paddle domain 112, a first substantially planar surface 114, a second substantially planar surface 116 opposite the first substantially planar surface 114, and a width 118 defined between first substantially planar surface 114 and second substantially planar surface 116. Compression paddle 100 has a grid domain 120, which includes at least one aperture 110 or perforation for inserting a biopsy needle through the compression paddle 100 as well as positioning means 122, 124 which aid in the positioning of a biopsy tool or biopsy needle. In an exemplary embodiment, at least one aperture 110 is in the shape or form of a circle, the y-coordinate positioning means 124 are numbers, and the x-coordinate positioning means 122 are letters. Positioning means 122, 124 on compression paddle 110 may be in any form that allows for accurate positioning of a biopsy tool or needle.

Referring to FIG. 3, FIG. 4, and FIG. 5, at least one aperture 110 may be of any shape or form which allows for a biopsy tool or needle to pass through the compression paddle 100, including but not limited to substantially circular, rectangular, square, hexagonal, polygonal, or linear apertures, or any combination thereof. The grid domain 120 of the compression paddle 100 may vary in size, for example, occupying less than about 15% of the paddle as shown in FIG. 4, less than about 40% of the paddle as shown in FIG. 3, less than about 50% of the paddle as shown in FIG. 5, or an even greater amount of the compression paddle 100 (not shown).

In one embodiment, the system comprises at least one marker 126. The at least one marker may be a small, radiopaque marker, which produces a limited artifact on or within a DBT image or a DBT image slice. In at least one embodiment, the at least one marker 126 may be formed as a grid (i.e. the marker may be as a grid in and of itself) or include a portion defining a grid. This grid may correspond, for instance, to a grid on compression paddle 100 or tool holder 200. The at least one marker 126 may be located on the compression paddle 100, on a tool holder, or both. The at least one marker 126 may be located on a surface parallel to the compression paddle 100 and/or on a surface non-parallel to the compression paddle 100. Though not limited to these locations or biopsies, the at least one marker 126 or grid located on the compression paddle 100 can allow for performance of a biopsy from the top of an object, whereas a marker or grid located on the tool holder 200 allows for biopsies to be performed from the top, side, or a lateral position of an object. The at least one marker 126 may be visible in a tomographic plane of a DBT reconstruction or reconstructed volume. In some embodiments, multiple paddle markers may be used. By using multiple paddle markers 126, for example three, possible angulations of the paddle in one or two directions can be determined by a machine or user.

Figure 6:
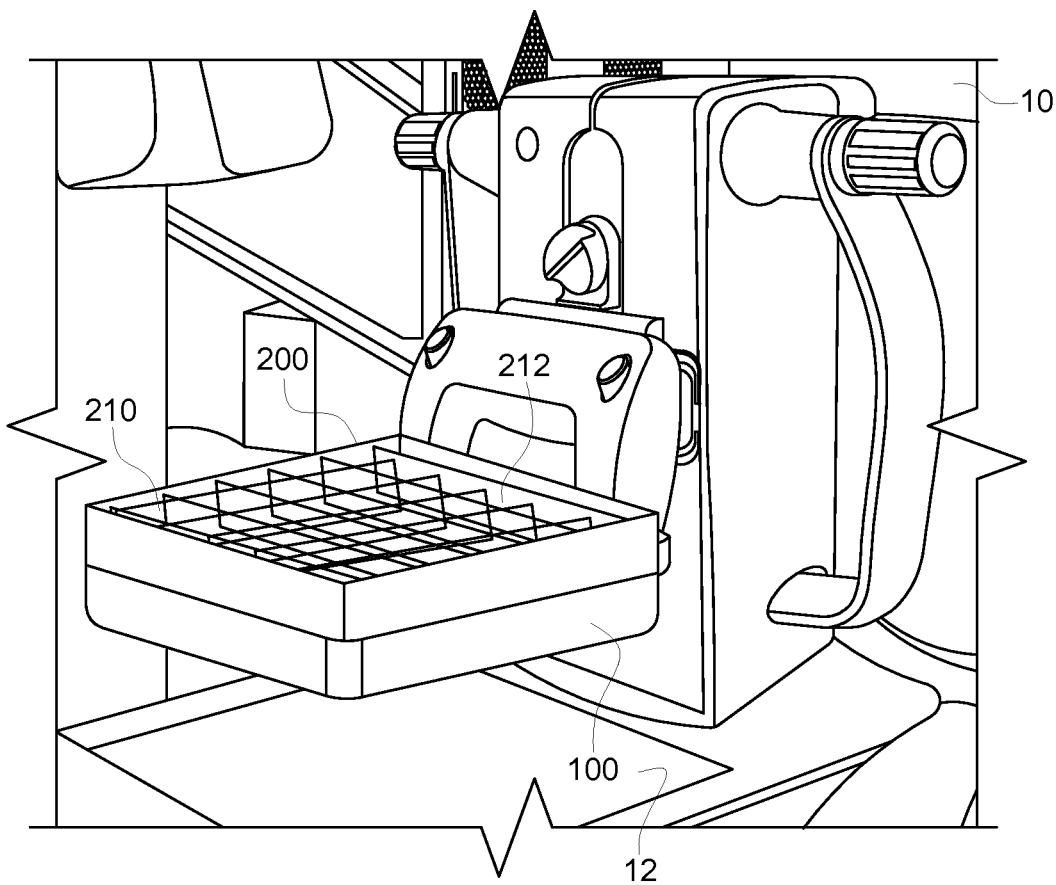
FIG. 6 illustrates a tool holder positioned on a compression paddle.

Referring to FIG. 6, FIG. 7, FIG. 8, and FIG. 9, means of positioning a biopsy tool on a tomosynthesis apparatus are shown. Referring to FIG. 6, the tool holder 200 is positioned on the compression paddle 100. In an embodiment, the tool holder 200 is made of a material that is strong enough in form to hold and position a tool, such as a biopsy tool, but does not distort or cause substantial artifacts in an x-ray image. In an embodiment, the tool holder 200 has at least one aperture 210, which aligns with the at least one aperture 110 in compression paddle 100. In another embodiment, the tool holder 200 substantially aligns with at least one aperture 110 in compression paddle 100. The tool holder 200 can include positioning means similar to or different from the positioning means on compression paddle 100 to allow for accurate positioning of a biopsy tool or needle on tool holder 200. In an embodiment, the tool holder 200 is in the form of a grid 212. The grid 212 can be in the form of plastic having walls of a height that can hold the biopsy tool and are thin so as to minimize the areas not accessible by the biopsy needle. In some embodiments, the grid 212 may be used to compress the object to be scanned while providing at least one aperture 110 to place the biopsy needle through.

Figure 15:
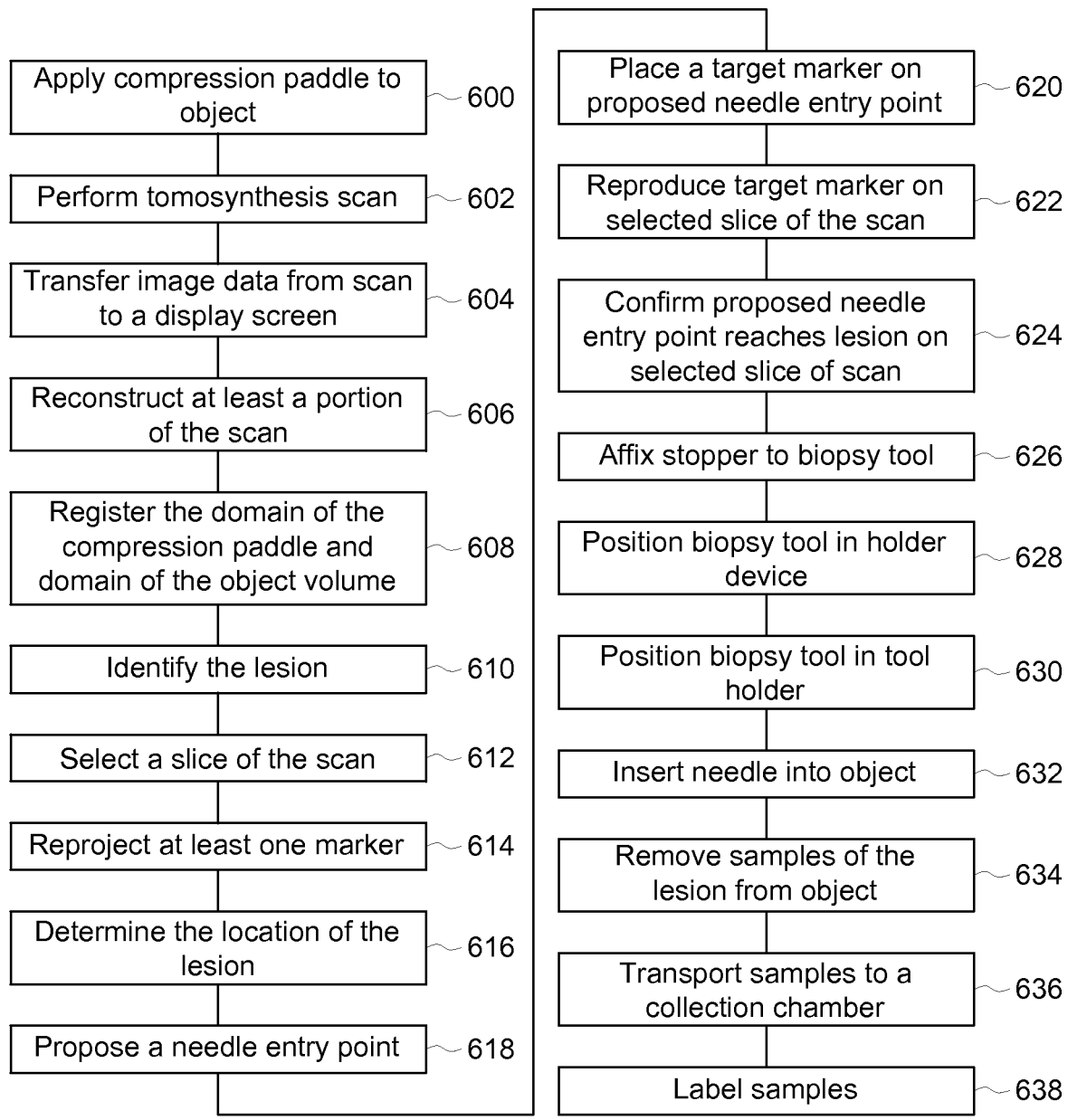
FIG. 15 is a flow chart depicting in detail the method of performing a guided breast biopsy using digital breast tomosynthesis.

In an embodiment, tool holder 200 is fixed to the compression paddle 100. Tool holder 200 may be fixed to the compression paddle 100 permanently if the tool holder 200 does not disturb the image acquisition and/or image reconstruction process in an undesirable manner or to an undesirable degree. In an embodiment, the tool holder 200 need not touch the breast. The tool holder 200 may be placed on top of the compression paddle 100 and function only to hold a biopsy tool. In another embodiment, the tool holder 200 may be part of the compression paddle 100, or even replace the compression paddle 100 as illustrated in FIG. 15. If the tool holder 200 generates no artifacts, it may be used to replace compression the paddle 100 and need not be removed prior to a scan being performed. In another embodiment, if the tool holder 200 does generate artifacts, it can be removed from the field of view of the scan, the scan may be performed, and the tool holder 200 may be replaced into the field of view afterwards. The geometry of the tool holder 200 is known by design, so its image or a comparable schematic representation can be synthesized for superimposition or reproduction, using the required transformation, with the tomographic slice demonstrating the biopsy target or lesion. If the tool holder 200 is removable, it should be replaced accurately and consistently.

The tool holder 200 may be located in any position which allows for the needle of a biopsy tool to reach the lesion or target of the biopsy. In an exemplary embodiment, the tool holder 200 is located just above or on top of the compression paddle 100, wherein once a biopsy tool is positioned in the tool holder 200, the needle of the biopsy tool will extend through an aperture in the compression paddle 100 to reach the target of the biopsy.

Figure 16:
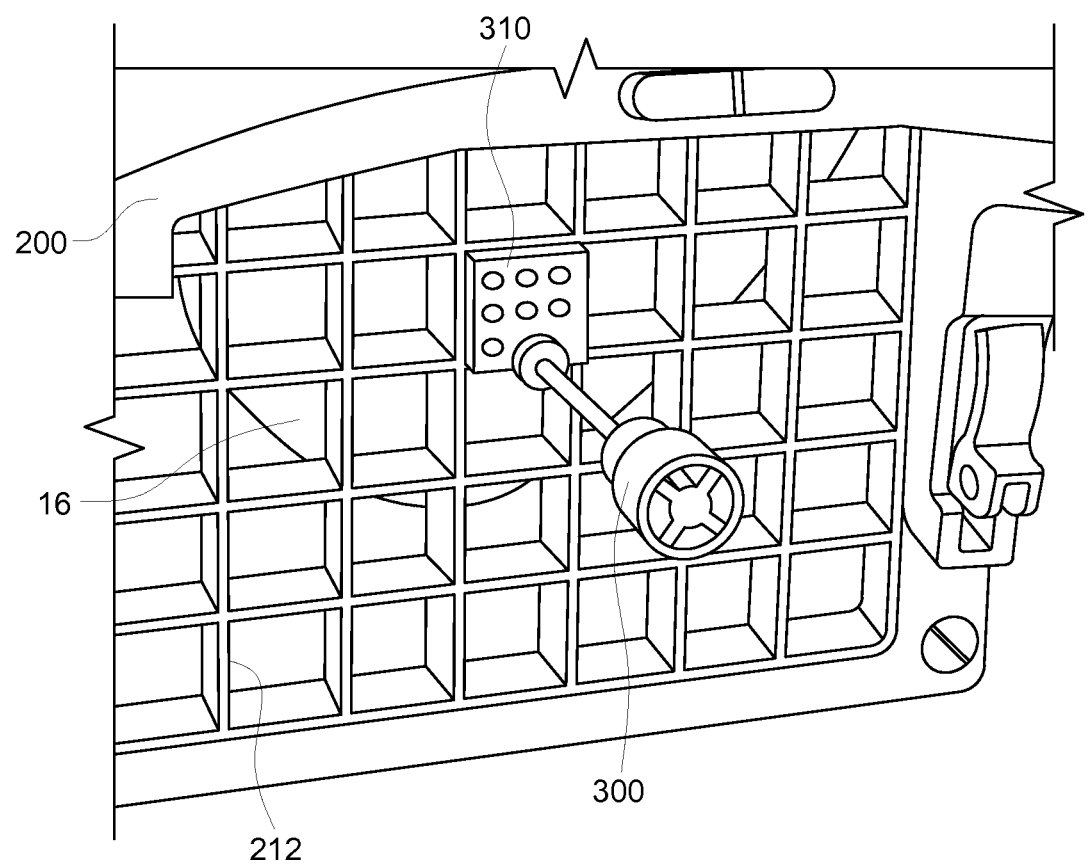
FIG. 16 illustrates an embodiment of a tool holder for performing a lateral biopsy.

Referring now to FIG. 16, an exemplary embodiment is illustrated of a lateral biopsy. In a lateral biopsy, the tool holder 200 is located on a side of the object 16 to be biopsied, to a side of the compression paddle 100, or substantially perpendicular to the compression paddle 100 or object 16. In this embodiment, once a biopsy tool 300 is positioned in the tool holder 200, the needle of the biopsy tool may extend into the object to be biopsied without passing through the compression paddle 100. Tool holder 200 may provide compression to the object, stability to the biopsy tool 300, and an aperture for which the biopsy tool 300 may pass through. Additionally, the holder device 310 may be used in the tool holder 200 to provide additional positioning means. In yet another embodiment, the tool holder 200 may be located at an opposite position as compression paddle 100, wherein the object to be biopsied may be positioned between the compression paddle 100 and the tool holder 200. In this embodiment, once the biopsy tool is positioned in the tool holder 200, the needle of the biopsy tool may extend into the object to be biopsied without passing through the compression paddle 100.

Figure 8:
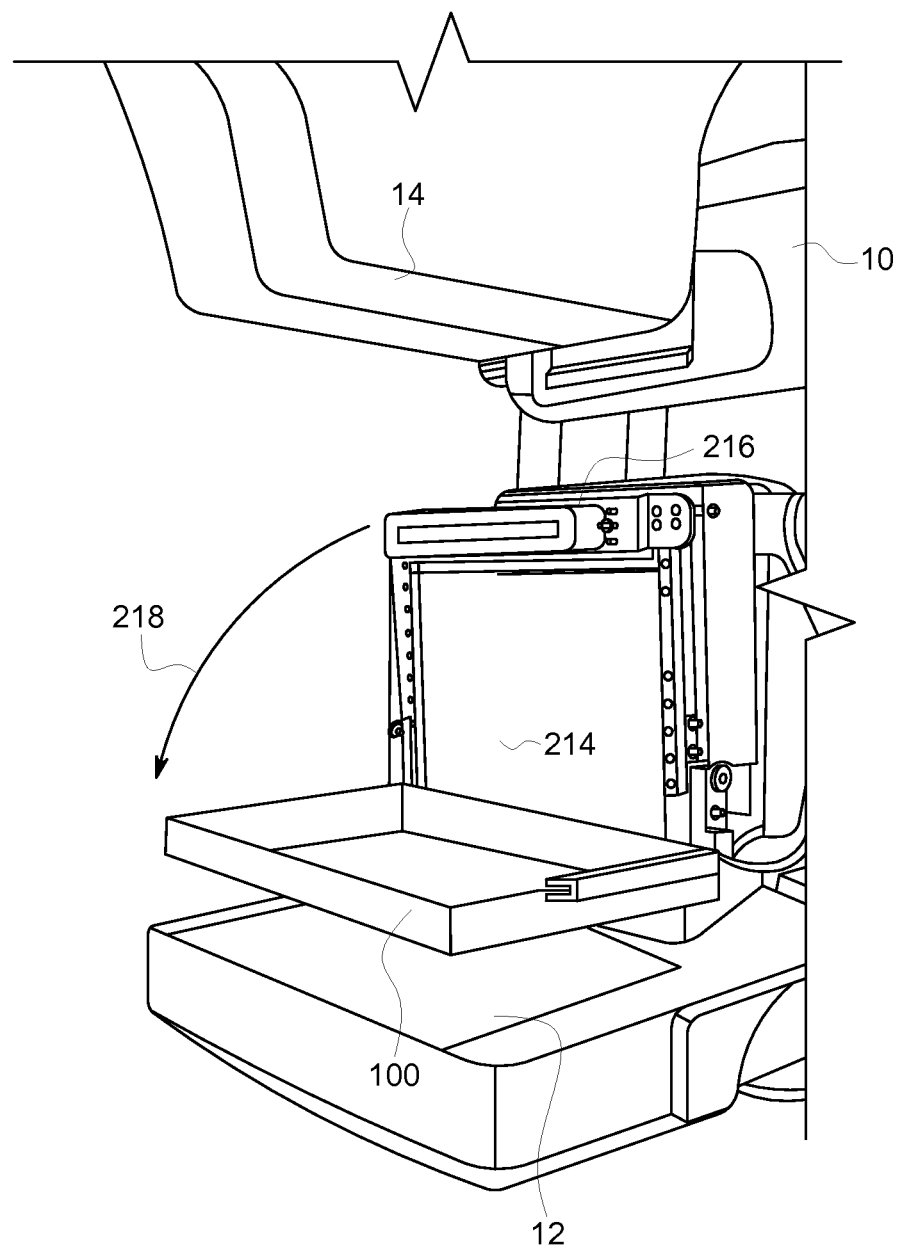
FIG. 8 illustrates a tool holder removed from the viewing field of the image acquired by the tomosynthesis system.
Figure 9:
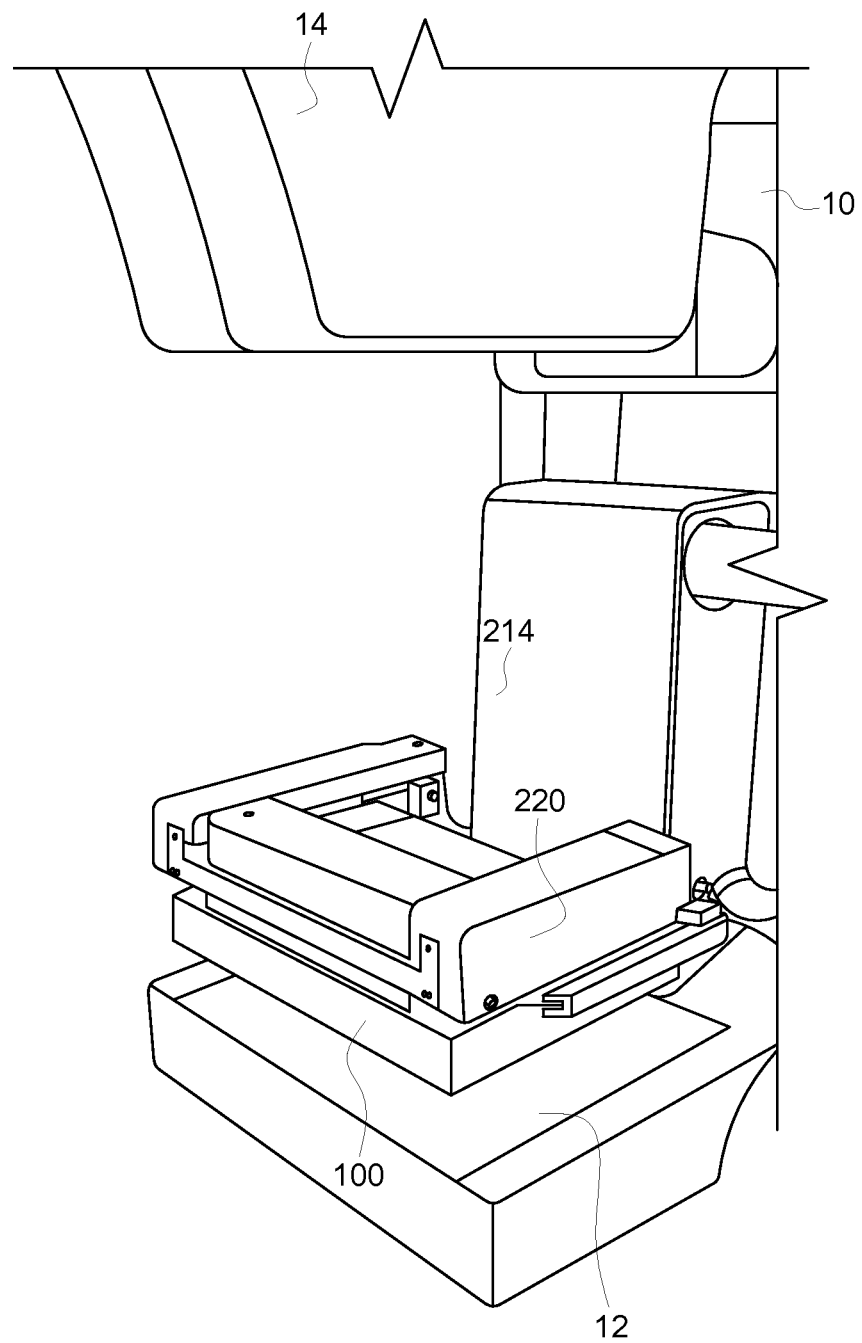
FIG. 9 illustrates a tool holder within the field of the image acquired by the tomosynthesis system.

Referring next to FIG. 8 and FIG. 9, means for moving the tool holder 200 into and out of an image frame or field of view are shown. In an embodiment, the tool holder 200 may optionally be removable from a field of view 214 during image acquisition to avoid artifacts in the reconstructed volume caused by the tool holder 200. FIG. 8 depicts the tool holder 200 in the "up" or a removed position 216, where the tool holder 200 will not appear in the image acquired by tomosynthesis apparatus 10. An arrow 218 depicts an optional path of movement of the tool holder 200 moving from the removed position 216 of FIG. 8 to a "down," established, or replaced position 220 of FIG. 9. The tool holder 200 may be fully or partially removed from the field of view 214 of the detector 12. It should be understood that in embodiments where the tool holder 200 is removed from the field of view 214, the tool holder 200 may be removed, detached, swiveled, rotated, or taken from the field of view 214 in any manner which eliminates at least a portion of the tool holder 200 from the field of view 214.

In one embodiment, where the tool holder 200 is removed from field of view 214 during image acquisition, it should is reinstalled after the image is acquired in a solid and reproducible manner. The reinstallation of the tool holder 200 can be accomplished by varying means such as by coordinating or aligning visible markers on the compression paddle 100, the tool holder 200, or both to align the compression paddle 100 with the tool holder 200, or the tool holder 200 with the compression paddle 100. In one embodiment, the compression paddle 100 and tool holder 200 both include visible markers, which are used to determine the unambiguous identification of the possible position of the biopsy tool on the tool holder 200. The desired accuracy and the accuracy achieved by the method and system discussed herein of the reinstallation of the tool holder is better than 5 mm and, more particularly, better than 1 mm.

Figure 7:
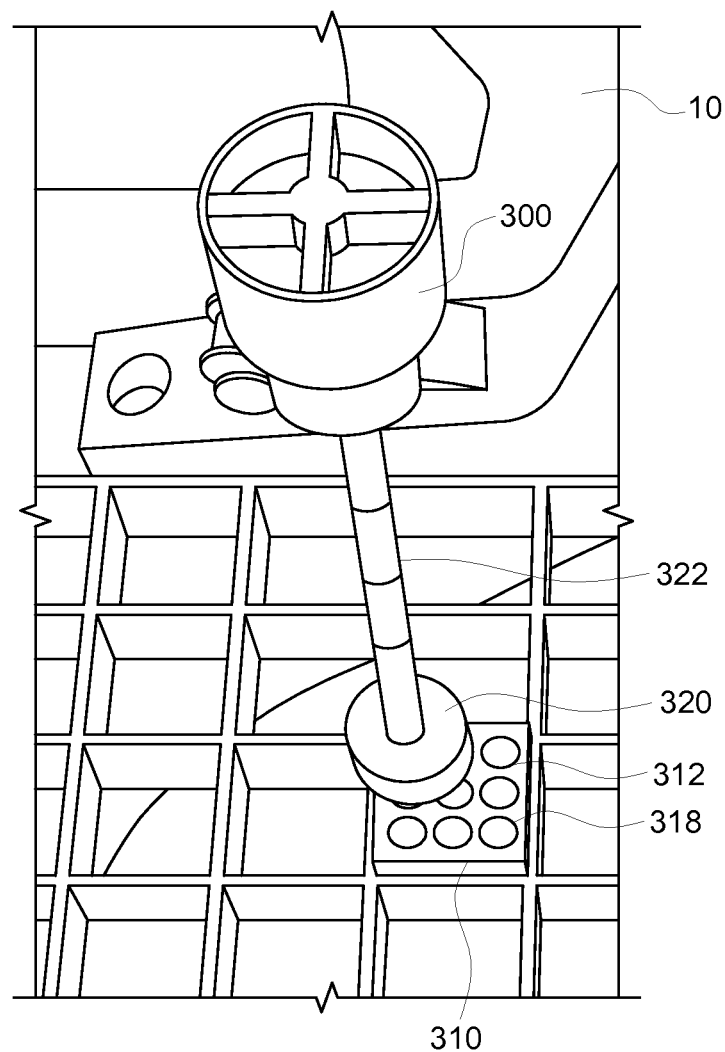
FIG. 7 illustrates an example of a biopsy tool positioned on a tool holder.

Drawing attention to FIG. 7, a tomosynthesis system may include a biopsy tool 300 and/or a holder device 310 used to perform the biopsy. A variety of tools may be used in the system, for example, a core needle or vacuum assisted biopsy tool. In an embodiment, the biopsy tool 300 may be positioned within the holder device 310 that provides a set of discrete positions for which the biopsy tool 300 may be positioned in one, two, or more directions. The holder device 310, also known as a "dice," may allow for discrete or intermediate positioning of the biopsy tool 300 aligned with an aperture relative to the position of the tool holder 200 and/or the compression paddle 100. The holder device 310 includes a first surface 312, a second surface 314 opposite the first surface 312, a width 316 defined between the first surface 312 and second surface 314 (not shown), and at least one aperture 318 extending from the first surface 312 to the second surface 314 of holder device 310 creating a passage or channel. In one embodiment, the tool holder 200 is in the form of a rectangular grid having rectangular apertures, and holder device 310 is in the form of a rectangle that sits within one aperture of the tool holder 200. In another embodiment, the holder device 310 is in the form of a square and is positioned one of the squares of the holder device 310, where the holder device 310 is subdivided into nine positions comprising nine apertures. At least a portion of the holder device 310 may be larger than the at least one aperture in the tool holder 200 or the holder device 310 may be smaller than the at least one aperture in the tool holder 200 and rest upon the compression paddle 100. The position of the holder device 310 aligns the biopsy tool 300 with an aperture 110 in the compression paddle 100 and an entry point at the surface of the paddle so that at least a portion of the biopsy tool 300 may enter the object to be biopsied through one aperture 110. In an embodiment, the portion of the biopsy tool 300 that passes through the compression paddle 100 is a needle that passes into a patient's breast.

A removable stopper 320 may be included on the biopsy tool 300 to provide for accurate needle positioning for a biopsy. In an embodiment, the exterior surface 322 of the biopsy tool 300 includes positioning means to indicate the depth at which the needle will be inserted into the object to be biopsied. In an embodiment, the positioning means are numerical and indicate millimeters. The stopper 320 may be fitted onto the exterior surface 322 of the biopsy tool 300 to position the biopsy tool 300 to extend into the object to be biopsied to a depth determined through identification of a target or lesion in tomosynthesis reconstruction. The stopper 320 may prevent the needle from extending past the target and thus missing the target, and may help to ensure the needle extends far enough to reach the target within the object to be biopsied. The stopper 320 may be in the form of a hard plastic, rubber, or similar material. In an embodiment, the stopper 320 is larger than the at least one aperture 318 in the holder device 310. The stopper 320 therefore holds the biopsy tool 300 steady and in place without shifting in any direction including up, down, or to a side, ensuring accuracy of the needle placement in the x, y, and z directions. In another embodiment, the stopper 320 is used directly on the tool holder 200 to position the biopsy tool without the use of the holder device 310.

As object 16 is compressed by the compression paddle 100, equipment capable of x-ray imaging, such as tomosynthesis apparatus 10, is used to acquire a scan 400 of the object 16. In one embodiment, the equipment is tomosynthesis equipment capable of performing a tomosynthesis scan of the object 16. In another embodiment, the equipment is a digital breast tomosynthesis system, which is capable of performing a DBT scan of a patient's breast. The scan 400 is performed for at least a portion of the object 16 using an x-ray system, and x-ray image data 410 is acquired.

At a high level, after a scan is performed, a user selects the tomographic slice or section where the potential lesion is visible. An image of a grid, marker, and/or tool support, or a schematic representation of a grid, marker and/or tool support is superimposed with the tomographic section after having been transformed. A user then identifies which of the apertures in the paddle and/or tool holder resides on the image and means are provided to identify which aperture in a holder device if used, also known as a dice, will give the best result. For example, numbers and letters may be used as shown in FIGS. 3-5. If a holder device 310 is being used, a reproduction of the holder device 310 may be shown or points representing the apertures of the holder device 310 may be shown in each aperture of the tool holder 200. In another embodiment, the user may select or designate an aperture in the holder device 200 using selecting means such as a mouse, and the holder device 310 may be shown for this aperture only.

Figure 10:
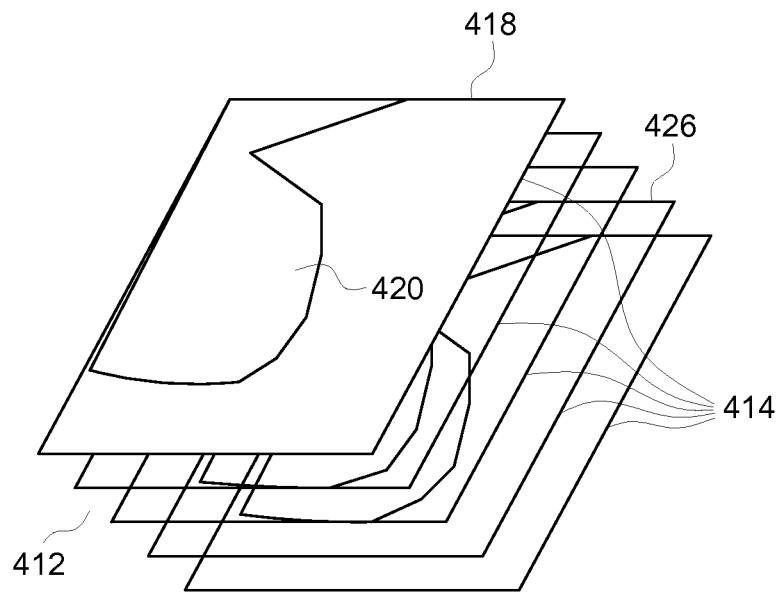
FIG. 10 illustrates a plurality of tomosynthesis slices.
Figure 11:
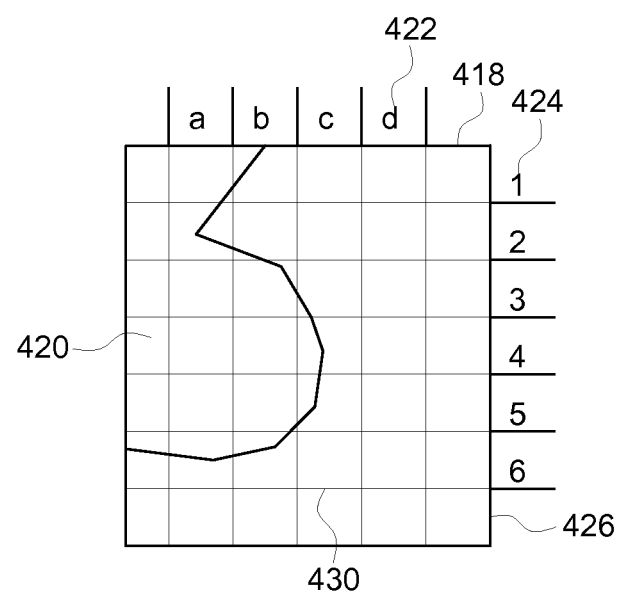
FIG. 11 illustrates a tomosynthesis slice with a reproduced grid.

Referring to FIG. 10, a reconstructed tomosynthesis reconstruction containing image data 410 of a volume 412 representing the object 16 may be displayed, or a portion thereof, as reconstructed slices 414 on a display screen 416. Display screen 416 may be located on the tomosynthesis apparatus 10, on a screen in communication with tomosynthesis apparatus 10, or on a remote screen.

In an embodiment, reconstructed slices 414 are displayed using a remote work station computer 415. The computer 415 is in communication with a data storage component and display screen 416, and is further capable of causing image data 410 to be reconstructed into the volume 412 or slices 414 and is displayed on the display screen 416. The data storage component may store data and operating parameters utilized by the computer to the tomosynthesis apparatus 10 and/or display and analyze the reconstructed slices 414. The data storage component may be in the form of a transient or fixed memory. The data storage component stores image data 410, which may be acquired by a tomosynthesis apparatus 10 connected to the computer or may be acquired through importing a scan performed at a remote location. The data storage component may also store software or algorithm codes used to operate the tomosynthesis apparatus 10, algorithms for reconstructing image data 410, and/or image data that has been constructed using the algorithms.

There is no limit or constraint for the method or system described herein on the sampling of the reconstructed volume 412 other than reconstructed volume 412 being known. The display screen 416 displays reconstructed slices 414, which may be displayed as a reconstructed volume 412, as an individual tomosynthesis slice 418, and/or as a group or set of tomosynthesis slices. The display screen 416 aids a user or machine in identifying a target or lesion 420 and in determining the location of the lesion 420. In one embodiment, the location of the lesion 420 is determined based upon the at least one grid or marker. The grid or marker may be an image of an actual grid or marker, a reprojection of a grid or marker, or a synthesized grid or marker. The transformation applied to the image or schematic representation of the grid, marker, or tool holder ensures that if the position selected coincides with the biopsy target, the needle will effectively reach the target. In another embodiment, the x-coordinate 422 and the y-coordinate 424 of the target may be identified using a grid 430 superimposed over a tomosynthesis slice 418. The z-coordinate of the lesion 420 corresponding to the depth of the lesion 420 is determined by analyzing or selecting a tomosynthesis slice 418. The z-coordinate of the individual tomosynthesis slice 418 may be perpendicular to a breast support.

Means allowing compression paddle 100 to be registered with respect to the volume 412 are present. In one embodiment, the registration means include numerical, alphabetical, or symbolic means to register the volume domain 428 with the paddle domain 112, with the tool holder 200, or both. In another embodiment, registration may be performed using a known relationship between the at least one marker 126 and the reproduced marker or markers visible on a tomosynthesis slice 418 to register volume domain 428 with paddle domain 112, with needle holder 200, or both. Any means that allow coordination or registration of the compression paddle 100 with volume domain 428 may be used. At least one marker 126 may be visible in slices of a volume parallel to the detector 12 or in slices of the volume non-parallel to the detector. In an embodiment, at least one marker 126 is at least partially visible in one or more slices of the reproduction in at least one orientation, and at least one slice is used from one or more additional orientations to locate the lesion or target.

In another embodiment, the set positions where the biopsy tool 300 may be fixed onto the tool holder 200 are represented in the plane of the tomosynthesis slice 418. In another embodiment, one marker determines the z-position and two, three, or more markers allow an operator to take into account possible angulations of the paddle in one or more directions. These markers may be in the form of radiopaque points visible in the volume domain 428 to allow full determination of its average plane. The markers may also be used to estimate the deformation of the paddle. In an embodiment, a marker or markers on the compression paddle 100 may be in the form of a disk within a circle, which allows for estimation of paddle deformation in order to accurately reproject location means onto the reconstructed tomosynthesis slice 418 or slices 414. The location means reprojected may be in the form of a grid 430.

The markers may vary in size, quantity, and/or shape, and allow for accurate reproduction on the tomosynthesis slices 414 or slice 418 of the compression paddle positioning means 122, 124 or compression paddle grid domain 120, or tool holder 200. The representation of the markers may be computed and take into account the geometry of the system and the possible angulations of the biopsy needle. The user or machine knows the orientation of the needle with respect to one or more of the compression paddle 100, biopsy tool 300, or tool holder 200. Knowing the angle will improve accuracy when positioning the needle in the position derived from image data 410 that corresponds to lesion 420, improving the likelihood lesion 420 will be reached by the needle.

In one embodiment, tomosynthesis slices 418 or slices 414 are reproduced based upon the at least one marker 126. In this embodiment, the slices are transformed or manipulated to account for variables such as deflection, paddle deformation, paddle tilt, etc. In another embodiment, the at least one marker 126 is transformed or reproduced to fit the reproduction of the slices. The at least one marker 126 may represent the tool holder 200, which may be transformed to fit the slices. In this embodiment, the at least one marker 126, which can be in the form of a grid or other shape, may be constructed according to one or more variables, such as deflection, paddle deformation, paddle tilt, etc. while the slice 418 or slices 414 are not manipulated. In these embodiments, where the reproduction of the slice 418 or slices 414 are transformed, or where the at least one marker 126 is transformed, an identified location of the at least one marker 126 is represented in superimposition with the lesion to be biopsied, and if a biopsy tool is positioned at the identified location, the needle will reach the lesion.

The operator of the tomosynthesis system may choose how and when to display the reprojection or reproduction of positioning means 122, 124 and/or grid domain 120. An operator may choose to hide or display the reprojection as the user determines based on the user's objective. In one embodiment, the reconstructed radiopaque paddle grid 430 may be reprojected on tomographic slices 414 or on an individual tomographic slice 418. In another embodiment, the grid is in a virtual form based off of known data corresponding to the grid and aligned using the marker 126.

Figure 12:
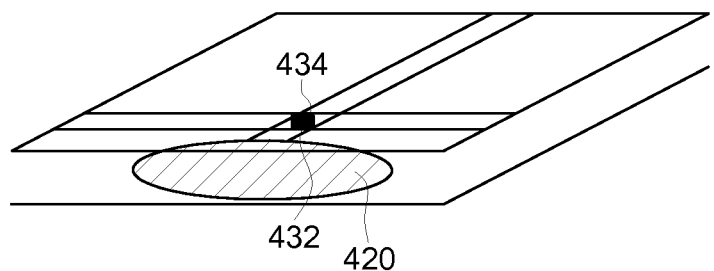
FIG. 12 illustrates a target marker placed on a proposed needle position on the tomosynthesis reconstruction.
Figure 13:
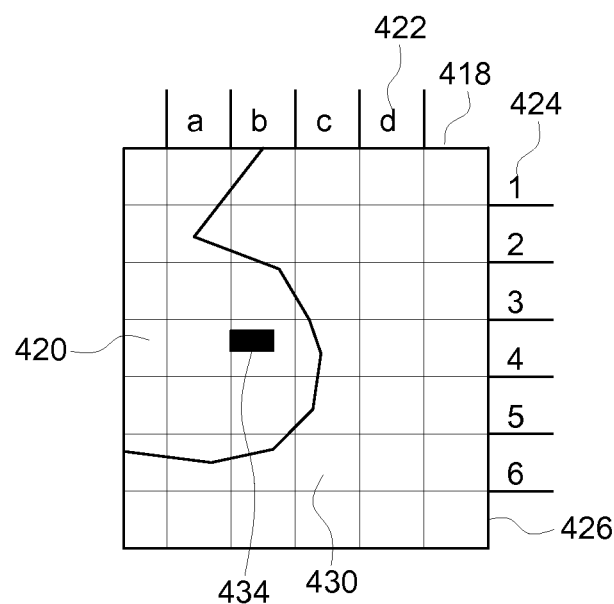
FIG. 13 illustrates a target marker corresponding to the proposed needle position within the target.

From the reprojection, the entrance point of the needle and depth to be used when the biopsy is performed can be determined. With reference to FIG. 12 and FIG. 13, z-coordinate 426 of the lesion 420 can be determined by selecting one or more of the tomographic slices 414, where the slice or slices selected correspond(s) to the z-coordinate 426. Based on the z-coordinate 426, the stopper 320 may be used to fix the depth to which the needle may be inserted into the object 16. Alternatively, threading may be used to fix the depth of the insertion of the needle.

In an embodiment, the location of entry point 432 of the biopsy tool 300 is determined by a basic computation of the location of lesion 420. In another embodiment, the entry point 432 of the biopsy tool 300 may be determined by building a relationship or correlation between the location of the lesion 420 and the at least one marker 126 to determine entry point 432, which will reach the location of the lesion 420 in the tomographic slices 414. Such locations may be in the form of coordinates, such as x and y coordinates.

In at least one embodiment, a controller is used to correlate the marker with the target or lesion 420. The controller may be in the form of a computer or processor having a memory and imaging processing capabilities. The controller can be used to generate a display or representation of the at least one marker on the reproduction. The controller may then form a relationship or correlation between the marker, the marker for example being grid 430, and the lesion 420 by computing the location of lesion 420. Based on this correlation, the controller may then propose the needle entry point 432. The controller may also be used to determine a relationship or correlation between the coordinates of the entry point 432 and the coordinate of the target lesion 420 in the tomographic slices 414.

In another embodiment, visual markers such as the grid domain 120 may be painted on the compression paddle 100 and/or needle holder 200 and overlayed onto tomographic slices 414 by the controller and displayed on a display screen. In generating a the grid display or projection, the controller takes into account paddle tilt/deformation and needle orientation such that there is a match between the coordinates in the plane using the grid and the original grid on which the needle will actually be positioned. The controller can notify the depth to the user, taking into account the geometry. Using the depth and the correlation to the target, the controller can propose a needle entry point. The user may then easily place the needle on the original grid or compression paddle having a grid. The controller may reconstruct the grid on the uppermost slice of the DBT volume or a synthetic grid may be displayed corresponding to the actual grid on the tool holder or compression paddle. Because of this, the original grid on the paddle and/or tool holder may or may not be radiopaque.

The x-coordinate, y-coordinate, and z-coordinates of the paddle domain 112 and the depth corresponding to the selected tomosynthesis slice 418 may be updated as the user moves a selection means from one slice to another slice or from one position on a slice to a different position on the slice. The x-coordinate and y-coordinate of the compression paddle 100 and/or the tool holder 200 may not be the same as the x-coordinate and y-coordinate of the lesion 420 and/or may not be the same as the x-coordinate and y-coordinate of entry point 432. Therefore, the coordinates of the lesion may be different from the coordinates of the proposed needle entry point. The coordinates may differ because the reprojected marker, markers, or grid may be based at least in part upon information about needle angulation, paddle deflection, paddle deformation, registration between a domain of the compression paddle with a volume of the tomosynthesis reconstruction (reconstructed volume), or any combination of information. By employing the system and/or method disclosed herein, the coordinates of the lesion can be checked or compared to a position on the tool holder 200 and/or compression paddle 100 to aid in positioning a biopsy tool to reach lesion 420.

In an embodiment, entry point 432 of the biopsy tool 300 may be determined using visual markers, which correspond to the at least one marker 126 on the compression paddle 100, tool holder 200, or both. In an embodiment, the entry point 432 of the biopsy tool 300 may be determined using a grid painted on compression paddle 100, which is reprojected over a tomosynthesis slice 418. Using the at least one marker 126, the virtual grid 430 is overlaid onto a tomosynthesis slice and displayed on display screen 416 or surface, such as the surface of the object of interest. The virtual grid 430 allows an operator or machine to take into account compression paddle tilt, deflection, deformation, needle angulations, and needle orientation such that there is a match between the coordinates in the plane using the virtual grid 430 and a compression paddle grid domain 120 or tool holder grid 212 where the biopsy tool will be positioned. The depth, taking into account geometry, is notified to the operator or machine. In an embodiment, the geometry is based upon a known needle angle and the determined x-coordinate and y-coordinate of lesion 420. The operator can then easily and simply position the biopsy tool 300 on the compression paddle 100 or in tool the holder 200. The virtual grid 430 on the tomosynthesis slice 418 or slices 414 may be a grid reconstructed on the uppermost slice of volume 412 or a grid reproduced on one or more of the tomosynthesis slices 414. A grid on compression paddle 100 or tool holder 200 may or may not be radiopaque.

Using reconstructed slices 414 and the at least one marker, an entry point 432 of the biopsy tool 300 may be determined or estimated by an operator or machine. With reference to FIGS. 12 and 13, in an exemplary embodiment, the location of the biopsy tool entry point 432 can be validated by an operator by placing a target marker 434 on the proposed or candidate entry point 432 location and performing another DBT image acquisition. Alternatively, a virtual marker may be placed on the proposed entry point 432 within the tomosynthesis slices 414. The validation confirms the target marker and the proposed entry point 432 derived from image data 410 match so that a biopsy needle will reach the target lesion prior to positioning or inserting biopsy tool 300.

The target marker 434 can be reconstructed using an acquisition in combination with previous acquisitions since the location of the target marker 434 is known in the z-position above compression paddle 100. A subtraction of a zero degree projection with and without the marker can confirm the location of lesion 420. In an embodiment, an actual reconstruction of the target marker 434 may be reprojected onto any tomosynthesis slice 418 or 2D view. The weight of the biopsy gun, the size of the biopsy gun, or both may be used to simulate similar paddle deformation to that which will be present when the biopsy is performed. Markers on the paddle, for example a disk in a circle, can allow estimation of paddle deformation in order to ensure accuracy during reprojection.

Once the entry point 432 of the biopsy tool 300 is determined, the biopsy tool 300 is positioned within the tool holder 200. In one embodiment, the tool holder 200 is used to hold the biopsy tool 300 straight and perpendicular to the plane of compression paddle 100. The biopsy tool 300 may then be used to insert a trocar point meant to penetrate a patient's skin and reach the lesion 420. The trocar point may be replaced with a tomography-compatible stylet, which can be similar in weight and size to a biopsy needle. If the user determines it is okay to proceed, the stylet is replaced with a biopsy needle.

Figure 17:
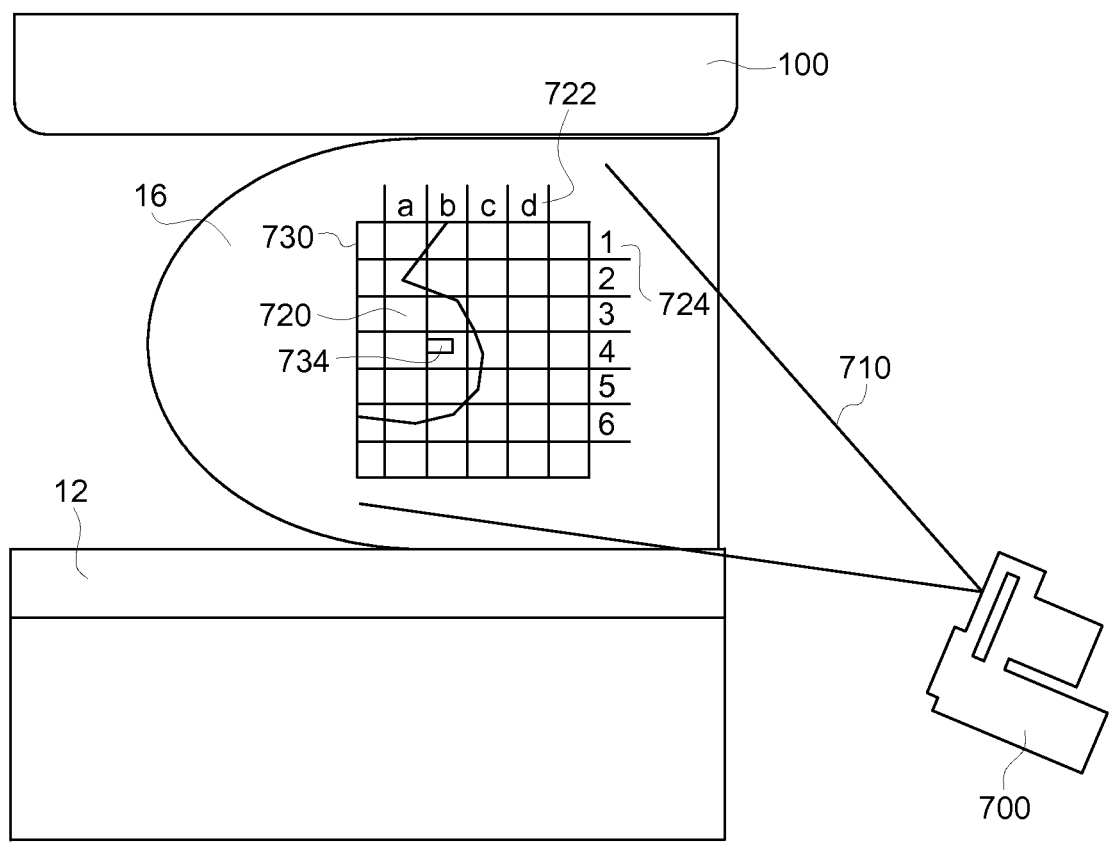
FIG. 17 illustrates a projection of a tomosynthesis slice onto an object to be biopsied.

Referring to FIG. 17, a projector 700 is shown displaying a projection 710 of a tomosynthesis slice on the object 16 to be biopsied. The projection 710 may be displayed in any form or in any manner that allows a user to identify a lesion and/or target. For example, the projection may be displayed on any surface, screen, monitor, object, and/or directly onto the skin of a patient. In at least one embodiment, a user may locate the lesion 720 on a display screen as previously described. The displayed slice 418 or slices 414 may be transformed using the at least one marker 126, and displayed on a surface, such the patient's skin, close to or coinciding with the proposed entrance point 734 using optical or projection means 700 such as "picoprojector" or any means which can produce a projection. The image of the selected DBT slice can be projected with a satisfactory light level (a few hundred lumens) with modern technology devices. This would allow any device to position the tool on the transformed image without any consideration of coordinates. The projection 700 would typically be displayed between the compression paddle 100 and detector 12. In another embodiment, the projector 700 may display the projection 710 onto the object 16, where the projection 710 also provides an image of a tool holder. Tool holder 200 may then be aligned, based upon the projection 710 and a biopsy tool fixed accordingly to align with an entry point.

An operator may select a portion of the 3D reconstructed volume containing the desired biopsy lesion 720. As a consequence of the transformation applied to the image, positioning the biopsy tool in coincidence with the image of the biopsy target will ensure that the target will be reached using a projection. The z-coordinate information will be determined from the entry point and the actual position of the biopsy target using the selected tomosynthesis slice 730. This embodiment would allow for accurate positioning of a biopsy tool based upon an image of the lesion projected onto the object 16 in the form of a tomosynthesis slice without needing to determine an aperture in a tool holder or holder device. Optionally, x-coordinates and y-coordinates, 722 and 724 respectively, may also be displayed to aid in positioning of the biopsy tool. These coordinates could allow for discrete or continuous, purely manual or power-assisted positioning of the biopsy tool. Angulation may also be provided to the tool holder with the displayed image being transformed accordingly. The tool holder 200 (not shown) may then be positioned with reference to the target 734, but without the need to determine a specific position or coordinates of a biopsy tool on the tool holder 200. A user would need only to position an aperture of the tool holder 200 in alignment with the target 734.

In an embodiment, biopsy tool 300 may be configured as a biopsy needle mounted to a handpiece. The biopsy needle may include an outer cannula, an inner cannula positioned therein, and an opening for receiving a portion of tissue from the biopsied lesion or target. The cannulas form a cutting device wherein the outer cannula is configured to slide or rotate over the inner cannula, and/or the inner cannula is configured to slide or rotate within the outer cannula. The biopsy tool may further comprise an introducer stylet and an introducer sheath mounted to the handpiece. The introducer stylet inserted within the introducer sheath is inserted into a patient.

Once biopsy tool 300 is inserted, at least one biopsy sample may be removed from the object 16, such as a patient's breast, by use of aspiration and/or the cutting mechanism formed by the inner and outer cannulas. The sample is moved by aspiration down an aspiration tube coupled to a collection chamber with, for example, individual pre-labeled chambers to delineate the order or location of each sample from the biopsy procedure. Alternative means of labeling each sample allowing for location identification and/or order identification may also be employed.

Figure 14:
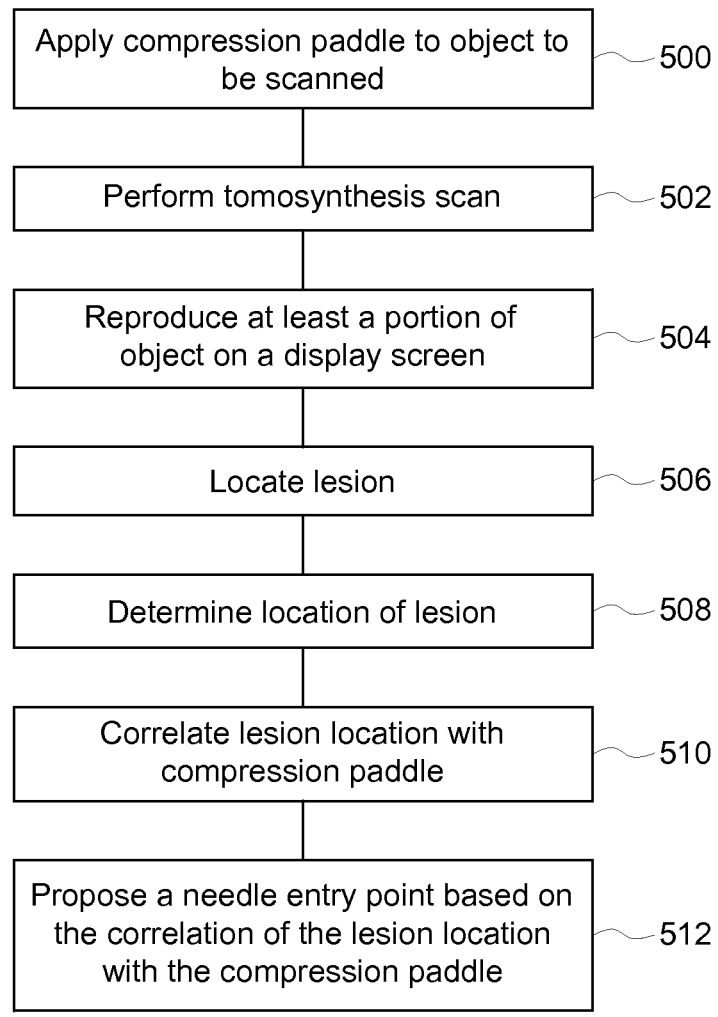
FIG. 14 is a flow chart depicting a method of performing a guided biopsy using tomosynthesis.

Referring to FIG. 14, a flow chart depicting an embodiment of a method of performing a biopsy is shown. In one embodiment, the method is performed on a patient undergoing a breast biopsy procedure, though not limited to a breast biopsy. At step 500 a compression paddle is applied to an object to be scanned. The compression paddle may have at least one aperture and at least one marker 126. The at least one marker 126 may be visible in a plane of a tomosynthesis reconstruction applied to an object to be scanned. A tomosynthesis scan is performed on at least a portion of the object at step 502. Following the scan, at least a portion of the object being scanned may be reconstructed or reproduced on a display screen at step 504. At step 506, the lesion or target may be located in the image of the scanned object. In an embodiment, once the lesion is located the at least one marker on the compression paddle may be used to determine a location or address of the lesion in the image at step 508. The location of the lesion may be correlated to the at least one marker 126 at step 510. Using the correlation between the lesion location 420 and the at least one marker 126, an entry point for a needle may be identified or proposed at step 512. Using this aforementioned method, if an insertion device such as a biopsy tool needle is positioned at the identified or proposed entry point, the device will effectively reach the lesion if it is properly inserted at said proposed or identified entry point.

Referring to FIG. 15, a flow chart depicting in detail an embodiment of a method of performing a biopsy is shown. A patient may be positioned in a tomosynthesis imaging system either standing, sitting, or laying down. Once the patient is positioned, a compression paddle is applied to the part of the patient to be scanned or the object to be scanned at step 600. In one embodiment, the compression paddle has at least one aperture and at least one marker on the compression paddle visible in a plane of a tomosynthesis reconstruction. In another embodiment, the compression paddle has at least three markers visible in a tomographic plane of the reconstruction. The marker may also be in the form of a grid painted on the compression paddle. The grid, marker, or markers may be radiopaque. In yet another embodiment, at least one marker visible in a plane of a tomosynthesis reconstruction may be located on a tool holder.

The tool holder may be affixed to the compression paddle or may be removable from the compression paddle. A user or machine may remove the tool holder from the field of view of the tomosynthesis scan prior to a scan being performed. Optionally, the tomosynthesis scan may be performed with the tool holder fixed to the compression paddle. If an initial tomosynthesis scan is performed without the tool holder in the field of view of the tomosynthesis scan, the tool holder may be replaced into the field of view and additional scans may be performed. The additional scans can allow a user or machine to identify the position on the tool holder corresponding to the lesion in the object.

A tomosynthesis scan of at least a portion of the object being scanned is performed at step 602. The tomosynthesis scan is transferred at step 604 to a display screen that is communicatively coupled to the tomosynthesis system that performed the scan. The display screen may be attached to a computer processing unit. In another embodiment, the tomosynthesis scan is acquired from another source, such as a memory. The other source may include a tomosynthesis scanning system located remotely from a display or computer system. For example, a scan may be sent to or from a first location such as a hospital, performing a scan to a second location, which can determine a proposed needle entry point remotely and transmit the same back to the first location.

Upon receiving the scan, at step 606 at least a portion of the tomosynthesis scan may be reconstructed on the display screen. At step 608, the domain of the compression paddle and the domain of the volume of the scanned object may be registered. In an embodiment, at step 610, the lesion or target is then identified by a user moving through a slice or a group of slices of the tomosynthesis reconstruction. Once the lesion is identified, a particular slice of the tomosynthesis reconstruction may be selected by the user at step 612 and the depth or z-coordinate of the lesion can be determined. If the user has not already done so, using the at least one marker on the compression paddle a user may reproject or reconstruct the marker over at least a portion of the scanned object at step 614. This reprojection is used to determine a location or address of the lesion at step 616. A relationship or correlation is then formed between the location of the lesion and a marker on the compression paddle or tool holder. In one embodiment, the location or address is an x-coordinate and a y-coordinate corresponding to the lesion, and a z-coordinate. From the z-coordinate, the x-coordinate, and the y-coordinate of the lesion, a correlation is drawn with a marker on the paddle and a needle entry point of a biopsy tool is proposed at step 618.

A user can confirm that the proposed needle entry point reaches the lesion using the tomosynthesis reconstruction. In an embodiment, the entry point of the needle or placement of the biopsy tool is confirmed by placing a target marker at step 620. The target marker may be positioned virtually onto the proposed entry point of the biopsy needle in the compression paddle. The target marker may then be projected or reproduced in a tomographic plane of the reconstruction at step 622 to determine if the entry point of the needle and the lesion or target correspond. If the lesion is missed, the process may be repeated until the target marker and the lesion correspond indicating that the needle position is correct and will reach the target of the biopsy.

Once the location of the needle entry point is determined and optionally confirmed, at step 624, a biopsy tool is prepared to be positioned in the biopsy tool holder. In an embodiment, a stopper is removably affixed at step 626 to the biopsy tool based off of the determined depth of the lesion. The stopper aids in ensuring the biopsy needle reaches the lesion and does not pass by the lesion or fall short of the lesion. In an embodiment, the biopsy tool may be positioned in a holder device at step 628, which will allow for intermediate positioning of the biopsy tool within the biopsy tool holder. At step 630, the biopsy tool is positioned in the biopsy tool holder. In an embodiment, the biopsy tool is positioned in the biopsy tool holder without any reference to the coordinates of the lesion. The biopsy tool may be positioned manually or by a machine or motor.

Once the biopsy tool is positioned, the biopsy tool is used to perform a biopsy of the object at step 632 by inserting the needle. In one embodiment, a biopsy needle is inserted in a portion of a patient to reach the lesion. In another embodiment, a trocar point is inserted to penetrate the patient's skin, the trocar point is then replaced by a stylet, and upon confirmation that it is okay to proceed, the stylet is replaced by a biopsy needle. In some embodiments the proposed needle entry point is projected or superimposed onto a surface of the object.

A sample or samples of the target of the biopsy may be removed from the patient at step 634. This may be done using aspiration, the cutting mechanism formed by the needle as discussed above, or a combination. At step 636, the samples may be transported to a collection chamber and may be labeled for later identification at step 638.

While illustrative embodiments have been described, it is noted that various modifications will be apparent to those of ordinary skill in the art in view of the above description and drawings. For the method described herein, it is to be understood that the steps may be performed in any order in alternative embodiments and may be repeated. Such modifications are within the scope of the disclosure, which is limited and defined only by the following claims.

What is claimed is:

1. A system comprising:
   a tomosynthesis imaging apparatus to perform a tomosynthesis scan and generate a digital breast tomosynthesis (DBT) volume comprising a plurality of image slices of an object, said apparatus comprising an x-ray source, an x-ray detector, and a computer;
   at least one marker;
   a compression paddle; and
   a display screen to display at least one of the plurality of image slices of the DBT volume generated by the imaging apparatus to locate a lesion location or target in the object,
   wherein (i) the computer superimposes an image of the at least one marker on at least one of the image slices of the DBT volume demonstrating the lesion location or target, and (ii) computer correlates the lesion location or target relative to the superimposed image of the at least one marker with the at least one marker itself placed on or near the compression paddle and determines a proposed needle entry point based on the correlation, the proposed needle entry point being a point where a needle or penetration device will effectively reach the lesion or target if it is inserted at said point.

2. The system of claim 1, wherein the at least one marker is located on the compression paddle.

3. The system of claim 1, further comprising a tool holder, wherein the at least one marker is located on the tool holder.

4. The system of claim 1, wherein the at least one marker is located on at least one of (i) a surface parallel to the compression paddle and (ii) a surface non-parallel to the compression paddle.

5. The system of claim 3, wherein the tool holder is located (i) on a surface parallel to the compression paddle or (ii) on a surface non-parallel to the compression paddle.

6. The system of claim 1, wherein the at least one marker is visible (i) in sections of a volume parallel to the detector or (ii) in sections of the volume non-parallel to the detector.

7. The system of claim 1, wherein the at least one marker is partially visible in one or more slices of the reproduction in one orientation, and where at least one slice is used from one or more additional orientations to locate the lesion.

8. The system of claim 1, wherein the at least one marker is reprojected based at least in part upon only (i) needle angulation, or only (ii) paddle deflection, or only (iii) registration between a domain of the compression paddle with a volume of the tomosynthesis scan, or any combination of (i), (ii), and (iii).

9. The system of claim 3, wherein the tool holder is moved at least partially out of a field of view of the x-ray detector during the tomosynthesis scan.

10. The system of claim 3, wherein the at least one marker is used to reproject a grid on at least a portion of the tomosynthesis scan.

11. The system of claim 1, wherein the superimposed image of the at least one marker is a virtual image generated by the computer.

12. The system of claim 1, wherein the system comprises a projector that is configured to project the proposed needle point onto a surface of the object.

13. A breast biopsy system comprising:
a tomosynthesis imaging apparatus to perform a tomosynthesis scan and generate a digital breast tomosynthesis (DBT) volume comprising a plurality of image slices of an object, said apparatus comprising an x-ray source, an x-ray detector, and a computer;
a marker or grid;
a compression paddle;
a biopsy needle; and
a display screen to display at least one of the plurality of image slices of the DBT volume generated by the imaging apparatus to locate a lesion location or target in the object,
wherein (i) the computer superimposes an image of the marker or grid on at least one of the image slices of the DBT volume demonstrating the lesion location or target, and (ii) the computer correlates the lesion location or target relative to the superimposed image of the marker or grid with the marker or grid itself placed on or near the compression paddle, and determines a proposed needle entry point of the biopsy needle based on the correlation, the proposed needle entry point being a point where a needle or penetration device will effectively reach the lesion or target if it is inserted at said point.

* * * * *